(12) United States Patent
Shelley et al.

(10) Patent No.: US 6,358,969 B1
(45) Date of Patent: Mar. 19, 2002

(54) 3-DESMETHYLRAPAMYCIN OR DERIVATIVES THEREOF, PROCESSES FOR THEIR PREPARATION AND THEIR USE AS ANTIFUNGAL AGENTS AND IMMUNOSUPPRESSANTS

(75) Inventors: Peter Robin Shelley, Betchworth; Rhona Mary Banks, Tadworth, both of (GB)

(73) Assignee: SmithKline Beecham p.l.c. (GB)

( * ) Notice: Subject to any disclaimer, the term of this patent is extended or adjusted under 35 U.S.C. 154(b) by 0 days.

(21) Appl. No.: 08/311,290

(22) Filed: Sep. 23, 1994

Related U.S. Application Data

(63) Continuation of application No. 08/107,736, filed as application No. PCT/GB92/00271 on Feb. 14, 1992.

(30) Foreign Application Priority Data

Feb. 19, 1991 (GB) .............................................. 9103430

(51) Int. Cl.$^7$ ................... C07D 498/18; C07D 491/16; A61K 31/445; A61K 31/395
(52) U.S. Cl. ...................................... 514/291; 540/456
(58) Field of Search ........................... 540/456; 514/291

(56) References Cited

U.S. PATENT DOCUMENTS

| | | | | |
|---|---|---|---|---|
| 3,993,749 A | * | 11/1976 | Sehgal | 424/122 |
| 5,091,389 A | * | 2/1992 | Oudeyka | 514/291 |
| 5,093,338 A | * | 3/1992 | Byrwe | 514/291 |

FOREIGN PATENT DOCUMENTS

| WO | WO 93/16189 | 8/1993 |
|---|---|---|

OTHER PUBLICATIONS

Verrall, M.S. "Discovery and Isolation of Microbial Products", 1985, E. Horwood Ltd, p. 22–29.*

Canadian Journal of Chemistry, vol. 60, No. 15, 1982, (Ottawa, CA), J.A. Findlay et al.: "The structure of demethoxyrapamycin", pp. 2046–2047, see abstract; compounds 1,2.

* cited by examiner

*Primary Examiner*—Bruck Kifle
(74) *Attorney, Agent, or Firm*—Yurly F. Stereho; Stephen Venetanner

(57) ABSTRACT

This invention provides 29-desmethylrapamycin of Formula I:

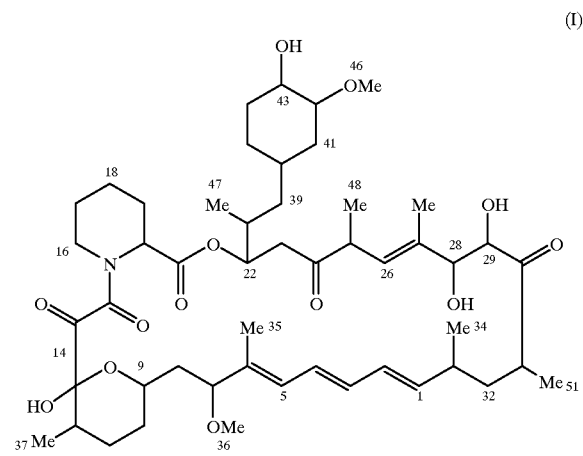

and a pharmaceutical composition thereof.

2 Claims, No Drawings

3-DESMETHYLRAPAMYCIN OR DERIVATIVES THEREOF, PROCESSES FOR THEIR PREPARATION AND THEIR USE AS ANTIFUNGAL AGENTS AND IMMUNOSUPPRESSANTS

This is a continuation of application Ser. No. 08/107,736, filed Oct. 19, 1993, which is a 371 of PCT/GB92/00271 filed Feb. 14, 1992.

The present invention relates to a novel compound and derivatives thereof, to processes for their production, to pharmaceutical formulations containing them, to their use in medical therapy, particularly in the treatment of bacterial and fungal infections, and also to their use as immunosuppressants.

Rapamycin is a known compound and was first isolated as an extract of the fungus *Streptomvces hygroscopicus* and reported to have antifungal activity (British Patent 1436447). Subsequently rapamycin has been implicated as an immunosuppressant (Martel R. R. et al Can. J. Physiol. Pharmacol. 55, 48–51, 1977).

A large number of microorganisms have been found to produce a variety of metabolites which have subsequently been isolated and have been shown to possess useful therapeutic properties. One such compound is 29-desmethylrapamycin. This is believed to be a novel compound and has been found to have useful antifungal activity and also immunosuppressant properties.

Accordingly the present invention provides 29-desmethylrapamycin and derivatives thereof.

The invention in a second aspect, further provides a process for the production of 29-desmethylrapamycin which comprises cultivating a producing microorganism and subsequently isolating 29-desmethylrapamycin or derivatives thereof.

29-desmethylrapamycin is believed to have the following structure:

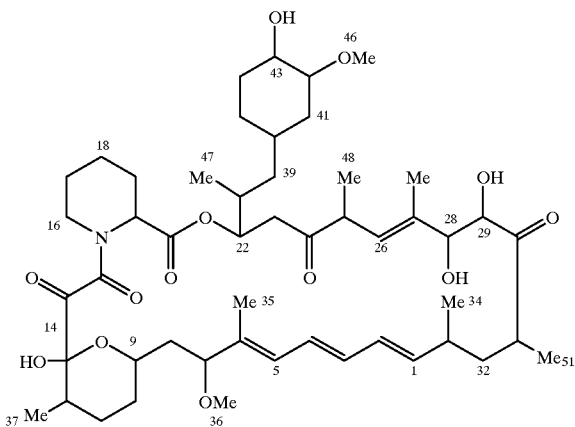

It has the following characteristics:
i) it has an apparent molecular weight of 899 by fast atom bombardment (FAB) mass spectroscopy,
ii) it may be obtained by the cultivation of a microorganism from the genus Streptomyces,
iii) $^{13}$CNMR spectroscopy reveals 50 carbons in the molecule,
iv) it shows antifungal activity against *Candida albicans*.
v) it shows immunosuppressant properties.

29-desmethylrapamycin may be obtained by the cultivation of a producing organism and the recovery of it or a derivative thereof from the culture.

The term 'cultivation' (and derivatives of that term) as used herein means the deliberate aerobic growth of an organism in the presence of assimilable sources of carbon, nitrogen, sulphur and mineral salts. Such aerobic growth may take place in a solid or semi-solid nutritive medium, or in a liquid medium in which the nutrients are dissolved or suspended. The cultivation may take place on an aerobic surface or by submerged culture. The nutritive medium may be composed of complex nutrients or may be chemically defined.

It has been found that suitable microorganisms for use in the cultivation process according to the invention include bacterial strains belonging to the genus Streptomyces which are capable of elaborating 29-desmethylrapamycin. It has further been found been isolated from nature and also mutants thereof.

The term 'mutant' as used herein includes any mutant strain which arises spontaneously or through the effect of an external agent whether that agent is applied deliberately or otherwise. Suitable methods of producing mutant strains including those outlined by H. I. Adler in 'Techniques for the Development of Microorganisms' in 'Radiation and Radioisotopes for Industrial Microorganisms', Proceedings of a Symposium, Vienna, 1973, page 241, International Atomic Energy Authority, and these include:
(i) Ionizing radiation (e.g. X-rays and γ-rays), u.v. light, u.v. light plus a photosensitizing agents (e.g. 8-methoxypsoralen), nitrous acid, hydroxylamine, pyrimidine base analogues (e.g. 5-bromouracil), acridines, alkylating agents (e.g. mustard gas, ethyl-methane sulphonate), hydrogen peroxide, phenols, formaldehyde, heat, and
(ii) Genetic techniques, including, for example, recombination, transformation, transduction, lysogenisation, lysogenic conversion, protoplast fusion and selective techniques for spontaneous mutants.

Using the methods of Becker B. Lechevalier M. P., Gordon R. E., Lechevalier H. A., 1964, Appl. Microbiol. 12, 421–423 and Williams S. T., Goodfellow M, Wellington E. M. H., Vickers J. C., Alderson. G., Sneath P. H. A., Sackin M. J., and Mortimer M. 1983 J. Gen. Microbiol. 129, 1815–1830, Sp. NCIB 40319 has been identified as a previously unreported, atypical, strain of Streptomyces and therefore also forms a part of the present invention, particularly in biologically pure form. It has been deposited at the National Collections of Industrial and Marine Bacteria Ltd. (N.C.I.B), Aberdeen, Scotland under number 40319 on Sep. 14, 1990.

Strain NCIB 40319 has been characterised as follows:
The method of whole-cell amino acid analysis was that described by Becker et al (1964). Identification media used for the characterisation of the culture were as described by Williams et al (1983). In addition, starch casein agar (Waksman S. A., 1961. The Actinomycetes Vol. 2 Williams and Wilkins Co. Baltimore ppl-363) was used for the morphological description of the culture.

The microorganism was characterised by inoculating agar blocks from a well grown plate into Y broth (see Table 1) and incubating for three days at 28° C. on a shaker. It was then centrifuged for 20 minutes at 3660 rpm, washed twice with distilled water, then finally resuspended in phosphate buffered saline (Dulbecco A). This inoculum was plated onto media commonly used for the identification of members of the Actinomycetales as above. Plates were incubated at 28° C. and the results were read at varying times but most were commonly taken at 14 days. The colours are described in common terminology but exact colours were determined by comparison with colour chips from the Methuen Handbook of colour (3rd Edn).

Results:

Cell Wall analysis

The whole-cell hydrolysates contained LL-diaminopimelic acid. The observations of growth and appearance of the organism were as follows:

Yeast extract-Malt extract Aear (ISP 2 Difco)

Growth good, cream 22a), with a white powdery centre. Colonies raised and rather wrinkled, no sporulation.

Inorganic Salts Starch Agar (ISP4 Difco)

Growth good, white with pale grey to grey (11b, 11c) aerial mycelium. Colonies quite flat with slightly raised centre. Reverse cream (22a).

Glycerol Asparagine Agar (S. A. Waksman, 1961, p328). medium No. 2.

Growth moderate to good, white with grey centre (11d) .Colonies flat, reverse cream (22a).

Starch Mineral Salts Agar

Growth very poor, opaque small colonies. No aerial mycelium.

Starch Casein Agar

Growth good, white with light grey to grey central area (11c, 11d), occasional small patch of white non-sporulating mycelium in grey sporulating areas. Tiny colourless droplets over the grey areas. Colonies fairly flat and gently rounded. Small black hygroscopic patches may occur after 4 weeks incubation.

Morphological Properties

These were observed after two weeks incubation on starch casein agar: spore mass in grey colour-series; spore chains in section spirales, tightly coiled or slightly open, of small diameter, generally 2–6 coils, occasionally more, may aggregate into hygroscopic masses. There was no fragmentation of vegetative mycelium.

Biochemical Properties

See Table 2 for full details. In summary, melanin not produced; nitrate not reduced to nitrite in organic nitrate broth; $H_2S$ produced in peptone-yeast extract iron broth; no growth on inhibitors; degradation only of arbutin, antibiosis only against *Bacillus subtilis*. Carbohydrate utilization glucose, cellobiose, fructose, inositol, mannitol, raffinose, rhamnose and xylose. Nitrogen sources used: asparagine, histidine and hydroxyproline, a-amino-butyric acid used only slightly.

Determination of Identification Scores

These were obtained using the Matiden program (Sneath P. H. A., 1979. Computers and Geosciences 5 195–213) which provides the best identification scores for known or unknown strains against the percent probability matrix of Williams et al (1983). Willcox Probability— the nearer the score reaches 1.0, the better is the fit of an unknown with a group in the matrix (scores of >0.85 acceptable) Taxonomic distance—low scores indicate relatedness (scores <0.3 acceptable). The organism had acceptable identification scores with cluster 32 (violaceoniger) which contains *Streptomyces hygroscopicus* species.

Conclusion

The culture is characterised by the grey spores in mass, the negative melanin reaction and the spores which are arranged in spirally coiled chains. The spore chains may coalesce into hygroscopic masses. The culture utilised a wide range of carbohydrate sources. The whole-cell hydrolysate indicates the presence of LL-diaminopimelic acid.

TABLE 1

| 1. Y broth | g/L |
| --- | --- |
| Special peptone (Oxoid) | 2.5 |
| Lab Lemco powder (Oxoid) | 2.5 |
| Tryptone (Oxoid) | 2.5 |
| Neutralized soya peptone (Oxoid) | 2.5 |
| Starch (BDH) | 2.5 |
| Glucose (BDH) | 2.5 |
| Malt Extract (Oxoid) | 2.5 |
| Glycerol (Fisons) | 2.5 |
| $GaCl_2.2H_2O$ (BDH) | 0.05 |
| $MgCl_2.6H_2O$ (Sigma) | 0.05 |
| NaCl (BDH) | 0.05 |
| $FeCl_3$ (Sigma) | 0.015 |
| $ZnCl_2$ (Sigma) | 0.0025 |
| $CuCl_2.2H_2O$ (Sigma) | 0.0025 |
| $MnSO_4.4H_2O$ (Sigma) | 0.0025 |
| $CoC_{12}.6H_2O$ (BDH) | 0.025 |

TABLE 2

Biochemical Characteristics of NCIB 40319

| Test | Result | |
| --- | --- | --- |
| Melanin production | − | |
| Use of Carbohydrates: | | |
| Adonitol | − | |
| Cellobiose | + | |
| D-Fructose | + | |
| Meso-Inositol | + | |
| Inulin | − | |
| Mannitol | + | |
| Raffinose | − | |
| L-Rhamnose | + | Willcox Probability |
| D-Xylose | + | |
| D-Glucose | + | Cluster 32 violaceoniger = 0.936 |
| Use of Nitrogen sources: | | |
| DL-a-Aminobutyric Acid | − | |
| L-Histidine | + | Taxonomic Difference |
| L-Hydroxyprohne | + | |
| Asparagine | + | Cluster 32 violaceoniger = 0.284 |
| Degradation of: | | |
| Allantoin | − | |
| Arbutin | + | |
| Xanthine | − | |
| Pectin | − | |
| Lecithin | − | |
| Nitrate Reduction | − | |
| $H_2S$ Production | + | |
| Growth on Inhibitors: | | |
| Sodium azide (0.01% w/v) | − | |
| NaCl (7.0% w/v) | − | |
| Phenol (0.1% w/v) | − | |
| Growth at 45° C. | − | |
| Antibiosis to: | | |
| *Aspergillus niger* | − | |
| *Bacillus subtilis* | + | |
| *Streptomyces murinus* | − | |

The fermentation medium for cultivating sp. NCIB 40319 suitably contains sources of assimilable carbon and assimilable nitrogen together with inorganic salts. Suitable sources of nitrogen include yeast extract, soyabean flour, meat extract, cottonseed, flour, malt, distillers dried solubles, amino acids, protein hydrolysates and ammonium and nitrate nitrogen. Suitable carbon sources include glucose, lactose, maltose, starch and glycerol. Suitably the culture medium also includes alkali metal ions (for example, sodium), halogen ions (for example, chloride), and alkaline earth metal ions (for example calcium and magnesium), as well as trace elements such as iron and cobalt.

The cultivation may suitably be effected at a temperature of about 20 to 35° C., advantageously 20 to 30° C., and the culture may suitably be harvested up to 7 days, advantageously about 3 to 5 days, after the initiation of fermentation in order to give an optimum yield of the desired product.

The desired product or a derivative thereof may then be isolated from the culture medium and worked up and purified using conventional techniques for such compounds. All such isolation and purification procedures may conveniently be effected at cool to ambient temperature, for example at a temperature within the range of from 4 to 40° C., conveniently from 20 to 35° C.

The desired compound may readily be identified in a routine manner by testing for antifungal activity and/or by monitoring the h.p.l.c. retention time.

Suitably, the separation procedure may include a high-performance liquid chromatography step, preferably as the last step. Elution may be effected using aqueous methanol.

29-desmethylrapamycin and its derivatives may be crystalline or non-crystalline and, if crystalline, may optionally be hydrated or solvated.

The derivatives are preferably pharmaceutically acceptable derivatives. Derivatives may include salts with pharmaceutically acceptable counter ions.

The compounds according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

29-desmethylrapamycin and its pharmaceutically acceptable derivatives have antifingal and immunosuppressant properties and are useful for the treatment of fungal infections in animals, especially mammals, including humans, in particular humans and domesticated animals (including farm animals). The compounds may be used for the treatment of topical fungal infections in man caused by, among other organisms, species of Candida, Trichophyton, Microsporum or Epidermophyton or in mucosal infections caused by *Candida albicans* (e.g. thrush and vaginal candidiasis). They may also be used in the treatment of systemic fungal infections caused by, for example *Candida albicans, Cryptococcus neoforma, Asperaillus fumigatus,* Coccidiodes, Paracocciciodes, Histoplasma or Blastastomyces spp. They may also be of use in treating eumycotic mycetoma, chromoblastomycosis and phycomycosis.

The compound of the invention is active as an immunomodulatory agent. The term "immunomodulatory agent" means that the compound of the invention is capable of inducing immune suppression by inhibiting T (and B) cell responses in vitro and/or by producing a statistically significant decrease in the inflammation system response medicated secondary lesion in the adjuvant induced arthritis. Indications for therapy using an immunomodulatory agent include, but are not limited to, the treatment of the following disease states:

rheumatoid arthritis
systemic lupus erythematosis
multiple sclerosis
acute transplantation/graft rejection
myasthenia gravis
progressive systemic sclerosis
multiple myeloma
atopic dermatitis
hyperimmunoglobulin E
hepatitis B antigen negative chronic active hepatitis
Hashimoto's thyroiditis
Familial Mediterranean fever
Grave's disease
autoimmune hemolytic anemia
primary biliary cirrhosis
inflammatory bowel disease
insulin dependent diabetes mellitus Accordingly the invention provides 29-desmethylrapamycin or derivative for use in medical therapy. Preferably for use as an antifungal agent or an immunomodulatory agent.

The invention further provides a method of treating a human or animal suffering from a fungal infection by the administration of an effective amount of 29-desmethylrapamycin or derivative thereof.

Moreover, the invention provides a method of treating a human or animal in need of immunomodulation by administration of an effective amount of 29-desmethylrapamycin or derivative thereof.

The invention further provides a pharmaceutical composition comprising a compound of the formula (I) or a pharmaceutically acceptable salt thereof together with a pharmaceutically acceptable diluent or carrier. The composition is preferably for human use in tablet, capsule, injectable or cream form.

For human use 29-desmethylrapamycin or derivatives thereof can be administered alone, but will generally be administered in admixture with a pharmaceutical carrier selected with regard to the intended route of administration and standard pharmaceutical practice. For example, they may be administered orally in the form of a tablet containing such excipients as starch or lactose, or in a capsule or ovule either alone or in admixture with excipients, or in the form of an elixir or suspension containing a flavouring or colouring agent. They may be injected parenterally, for example, intravenously, intramuscularly or subcutaneously. For parenteral administration, they are best used in the form of a sterile solutions which may contain other substances, for example, enough salts or glucose to make the solution isotonic.

For oral and parenteral administration to human patients suffering from a fungal infection, it is expected that the daily dosage level of the antifungal compounds of formula (I) will be from 0.1 to 10 mg/kg (in divided doses) when administered by either the oral or parenteral route. Thus tablets or capsules of the compounds can be expected to contain from 5 mg to 0.5 g of active compound for administration singly or two or more at a time as appropriate. The physician in any event will determine the actual dosage which will be most suitable for an individual patient and will vary with the age,,weight and response of the particular patient. The above dosages are exemplary of the average case. There can, of course, be individual instances where higher or lower dosage ranges are merited, and such are within the scope of this invention.

Equally for a human patient in need of immunomodulation the daily parenteral or oral dosage regimen for the compound or derivative thereof will preferably be from 0.1 mg/kg to 30 mg/kg.

No unacceptable toxicological effects are expected when the compound is administered in the above mentioned dosage ranges.

The compounds and compositions according to the invention may be formulated for administration in any convenient way for use in human or veterinary medicine, by analogy with other antifungal or immunomodulatory agent.

The compounds and tablets and capsules for oral administration may be in unit dosage form, and may contain conventional excipients including, for example, binding agents, for example, syrup, acacia, gelatin, sorbitol, tragacanth, or polyvinylpyrrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, propyleneglycol. The compound, depending on the vehicle and concentration used, may be either suspended or dissolved in the vehicle. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

The following examples serve to illustrate the present invention.

Preparation of 29-Desmethylranamycin

A culture producing 29-desmethylrapamycin has been classified as Streptomyces sp. and has been deposited in the National Collection of Industrial and Marine Bacteria, 23, St. Machar Drive, Aberdeen AB2 1RY, Scotland, UKI under the accession number NCIB 40319.

The culture was isolated from a termite hill at Abuke, Gambia.

EXAMPLE 1

Inoculum Preparation

Sporulating cultures grown on starch/casein agar (SCA) [Soluble starch (BDH) 10 g/L; casein (white soluble), 1 g/L; $K_2HPO_4$, 0.5 g/L; $MgSO_4$ $7H_2O$), 0.5/L; agar technical (Oxoid No.3) 18 g/L] in Roux bottles were treated with 50 ml 0.02% Tween 80 to produce a spore suspension. 7.5 ml spore suspension was inoculated into 400 ml RS1 medium (Soy peptone 10 g/L; Glucose monohydrate 20 g/l; bakers yeast 5 g/L; NaCl, 2 g/L; $ZnSO_4$ $7H_2O$, 0.05 g/L; $MgSO_4$ $7H_2O$, 0.125 g/L; $MnSO_4.4H_2O$, 0.01 g/L; $FeSO_4. 7H_2O$, 0.02 g/L] adjusted to pH7 with 5N sodium hydroxide. A 2 L shaken flask was used, incubated at 25° C., 240 rpm (50 mm throw).

Final Stare Fermentation

15 L RP2 medium [Soypeptone, 10 g/L; Glucose, 20 g/L; bakers yeast, 6 g/L; NaCl, 5 g/L; L Lysine monohydrochloride, 6 g/L; $K_2HPO_4$, 2.5 g/L; $KH_2PO_4$, 2.5 g/L; $MgSO_4$. $7H_2O$, 0.125 g/L; $ZnSO4$ $7H_2O$, 0.05 g/L; $MnSO_4$ $4H_2O$, 0.01 g/L; $FeSO_4.7H_2O$, 0.02 g/L; Glycerol 30.0 g/L; Soya Bean Oil, 20 g/L] together with 0.5 g/L NOPCO Foamaster antifoam was sterilised in situ in a 20 L fermenter at 121° C. for 45 minutes. The pH was adjusted to 6.4 after sterilisation with 50% $NH_3$ solution then inoculated at 4% with 72 hour seed culture. The fermenter was run at 25° C., 480 rpm with an airflow of 7.5 L/min at 0.2 bar overpressure. The pH was allowed to drop to 6.0 and was then maintained at that level by addition of 50% $NH_3$ solution. Foaming was controlled by addition of Pluronic L81 antifoam (20% solution in soyabean oil). The broth was harvested at 118 hours.

Isolation Procedure

At harvest whole broth (15 L) was adjusted to pH4 with sulphuric acid and the result centrifuged in batches at 2000 g for 20 minutes. The mycelial solids were extracted by soaking in dichloromethane overnight at 5° C. followed by mixing for 1 hour using a bladed stirrer.

Solids were removed by filtration (Whatman GFD paper) and the liquid phase concentrated to a thick oil using a rotary evaporator. The oil was extracted using methanol and the methanolic phase concentrated to a light oil. 60 ml of 15:85 acetone-hexane were added prior to silica chromatography.

Chromatographic Purification

The solution was chromatographed on a column 30×2.5 cm of silica gel (Sorbsil C60 Rhone-Poulenc, Manchester) packed in 15:85 acetone-hexane eluting with step gradient of acetone in hexane. Fractions obtained using greater than 30% acetone containing 29-desmethylrapamycin were combined and concentrated in vacuo to give 333 mg of an oil. Other fractions containing rapamycin were set aside.

The oil containing 29-desmethylrapamycin was dissolved in 2.2 ml of methanol and clarified by centrifugation at 2000 rpm. The supernatant was purified via preparative reverse phase high performance liquid chromatography (hplc). A Dynamax 60A $C_{18}$ column (41.4×250 mm) and a precolumn (41.4×50 mm), (Rainin Instruments Woburn, Mass. 01801, USA) was used. The column was eluted with methanol—water (72:28) at 50 ml/min. Elution was monitored at 275 nm. Fractions containing 29-desmethylrapamycin were pooled and evaporated to dryness, 23 mg of white powder were obtained. Fractions containing the object compound were analysed by reverse phase hplc using a microsorb 5 μm $C_{18}$ column 4.6×250 mm, (Rainin Instruments) with a 2.0×20 mm precolumn (Upchurch Scientific Ltd., Oak Harbour, Wash., 98277, USA) operated at 30° C. and monitored by ultraviolet absorbance at 275 nm. The column was eluted with methanol-water (78:22) at 1 ml/minute. Under these conditions the object compound designated 29-desmethylrapamycin had a retention time of 10.84 minutes, differing from that of rapamycin.

The resulting compound was characterised by mass spectroscopy (FAB)[M+Na]$^+$=922 and by proton and $^{13}C$ nuclear magnetic resonance spectroscopy. (see example 2 below), UV spectroscopy shows UV$\lambda_{max}$ in aqueous methanol at 269, 278 and 291 nm.

EXAMPLE 2

Inoculum Preparation

The procedure followed in Example 1 was used.

Final Stage Fermentation

300 L RP2 medium (plus NOPCO Foamaster antifoam, 0.5 g/L) was sterilised in i in a 450 L fenmenter at 121° C. for 60 minutes. The pH was adjusted to 6.4 with 50% $NH_3$ solution and then inoculated at 4% with 48 hour seed culture. The fermenter was run at 25° C., 220 rpm (110 rpm between 1 and 18 hours) with an airflow of 150 L/min at 0.5 bar overpressure. The pH was allowed to drop to 6.0 and was then maintained at that level by addition of 50% $NH_3$ solution. Foaming was controlled by addition of Pluronic L81 antifoam (20% solution in soyabean oil). The broth was harvested at 137 hours.

Isolation Procedure

At harvest whole broth (320 L) was adjusted to pH 4 with hydrochloric acid and the result fed at 3 L/minute to a Westfalia SA7-03-076 liquid/solid centrifugal separator (Westfalia Separator Ltd., Oelde W Germany). The accumulated solids were discharged intermittently to form a thickened slurry. This was extracted by stirring with 120 L of dichloromethane for 1 hour. The solvent phase was recovered by centrifugation (Sharples supercentrifuge) and the solids extracted again with 100 L of dichloromethane by stirring together for 12 hours. The solvent phase from the second extraction was separated by gravity and combined with the first solvent extract. The combined extract was concentrated in vacuo keeping the temperature below 35° C. to give 4 L of black oil and some suspended solids. Gross impurities were removed by multiple partitions (11) of the oil and solids against methanol. In all 62.4 L of rich methanol phase were recovered by gravity separation. This was concentrated to give 0.65 L of black oil.

Initial Chromatogaphic Purification

An equal volume of acetone-hexane 15:85 was added to the oil and the result loaded on a silica column (10×30 cm Sorbsil C60 silica 40–60 μm (Rhone-Poulenc) packed in acetone-hexane (15:85). Elution was carried out at 0.2 bar using an acetone-hexane step gradient. Fractions obtained using greater than 20% acetone contained rapamycin and were set aside. Fractions obtained using greater than 25% acetone containing 29-desmethylrapamycin were combined and evaporated to give an oil. This was dissolved in diethyl ether and some impurity precipated at 5° C. The remaining solution was evaporated to an oil and chromatographed on silica.

Chromatographic Purification

After loading the oil on a silica column (2.5×25 cm) packed with Sorbsil C60 silica 40–60 μm (Rhone-Poulenc) in 15:85 acetone-hexane, elution continued with 25:75 acetone-hexane. Fractions containing 29-desmethylrapamycin were pooled and concentrated in vacuo to give a residue. This was dissolved in methanol and further purification achieved via preparative hplc. A Dynamax-60 Å $C_{18}$ column (41.4×250 and pre column 41.4×50 mm, Rainin Instruments) was used. The column was eluted with methanol-water 72:28 at 50 ml/min. Elution was monitored at 275 nm. Fractions containing the object compound were pooled and concentrated in vacuo to give a white solid.

Final purification was achieved by preparative hplc using a Microsorb $C_{18}$5 μm column (21.4×250 mm) (Rainin Instruments). The column was eluted with methanol-water 74:26 and repetitive injection was used to purify all the product from the previous column. Fractions containing pure 29-desmethylrapamycin were pooled and concentrated in vacuo to yield a white solid. After further drying in vacuo 198.9 mg of 29-desmethylrapamycin were obtained. Fractions containing the object compound were analysed by reverse phase hplc using a Microsorb 5 μm $C_{18}$ column 4.6×250 mm (Rainin Instruments) and an Upchurch precolumn (2.0×20 mm). This system was operated at 30° C. and monitored by ultraviolet absorbance at 275 nm. The column was eluted with methanol-water 76:24 at 1 ml/minute. Under these conditions the object compound designated 29-desmethylrapamycin had a retention time of 13.8 minutes, differing from that of rapamycin.

29-desmethylrapamycin was characterised by mass spectroscopy FAB [M+Na]$^{+=922,}$ and by proton and $^{13}C$ nuclear magnetic resonance spectroscopy.

Antifungal Activity of 29-desmethylrapamycin

Spectrum of Activity

Method—The spectrum of activity was determined by placing solutions of the compound, prepared in sodium phosphate buffer, pH 6.6, in wells in seeded Sabouraud's Dextrose Agar. Activity was assessed by measuring the zones of inhibition following incubation at 37° C. (yeasts and *Aspergillus niger*) or 30° C. (other filamentous fungi) for 24 hours.

Results—(Table 1) The compound of the present invention has broad spectrum activity in the agar diffusion test.

MIC Data

Method—The Minimal Inhibitory Concentration (MIC) was determined by diluting the compound in a broth medium in a microtitre tray. The organisms were diluted and added to the wells to provide a final inoculum of approximately $10^5$ cells per ml or $10^4$ fungal spores per ml. The trays were incubated at 37° C. and the turbidity of each well noted at intervals. The (MIC) was taken as the lowest concentration (in mg/ml) which prevented significant growth.

Results—See Table 2.

TABLE 1

ZONES OF INHIBITION - (DIAMETER mm)
SCREEN TYPE 107

| COMPOUND | CONC µg/ml | Candida albicans 73/079 SAB | Crytococcus neoformans 451 SAB | Saccharomyces cerevisiae SAB | Aspergillus niger SAB | Hendersonula torulides TH65 SAB | Paecilomyces varioti SAB | Trichophyton mentagrophytes 569A SAB | Rhizopus oryzae 21602 SAB | Pityrosporum- canis 0024RE SAB |
|---|---|---|---|---|---|---|---|---|---|---|
| 29-Desmethyl rapamycin | 500 | 29a | 29b | 33a | 47a | 36a | 28b | 43a | 47a | 0 |
| | 100 | 29a | 29b | 34a | 46a | 33a | 26b | 42a | 46a | 0 | a = hazy-edged zone
b = whole zone hazy

TABLE 2

Minimum Inhibitory Concentration (µg/ml)

(determined after 1 and 2 days incubation)

| ORGANISM* | DAY | MIC |
|---|---|---|
| *Candida albicans* | 1 | 32 |
| 731079 | 2 | 32 |
| *Aspergillus niger* | 1 | 16 |
| | 2 | 32 |

*Inoculum $10^5$ cells/ml and $10^4$ spores/ml, respectively

What is claimed is:

1. A compound of formula (I):

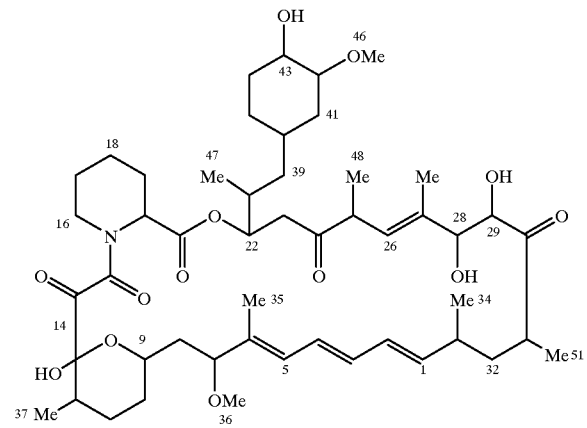

which is 29-desmethylrapamycin.

2. A pharmaceutical composition comprising a compound according to claim 1 together with a pharmaceutically acceptable carrier or excipient.

* * * * *